United States Patent
Ellis et al.

(10) Patent No.: US 7,361,359 B2
(45) Date of Patent: Apr. 22, 2008

(54) NEOSPORA CANINUM ISOLATE

(75) Inventors: John Timothy Ellis, Hornsby (AU); Catherine Margaret Douglas Miller, Roseville (AU); Helen Elizabeth Quinn, Lane Cove (AU)

(73) Assignee: University of Technology, Sydney, New South Wales (AU)

( * ) Notice: Subject to any disclaimer, the term of this patent is extended or adjusted under 35 U.S.C. 154(b) by 0 days.

(21) Appl. No.: 10/332,387

(22) PCT Filed: Jul. 27, 2001

(86) PCT No.: PCT/AU01/00908

§ 371 (c)(1), (2), (4) Date: Apr. 4, 2003

(87) PCT Pub. No.: WO02/10340

PCT Pub. Date: Feb. 7, 2002

(65) Prior Publication Data

US 2003/0185852 A1    Oct. 2, 2003

(30) Foreign Application Priority Data

Jul. 28, 2000    (AU) .................................. PQ9056

(51) Int. Cl.
*A61K 39/00* (2006.01)
*A61K 39/008* (2006.01)
*A01N 63/00* (2006.01)

(52) U.S. Cl. ............... 424/265.1; 424/93.1; 424/269.1; 424/184.1

(58) Field of Classification Search ............... 424/93.1, 424/269.1, 265.1, 184.1
See application file for complete search history.

(56) References Cited

U.S. PATENT DOCUMENTS 5,942,394 A     8/1999  Ellis et al. ...................... 435/6
6,656,479 B2 * 12/2003  Brake et al. ............. 424/269.1

FOREIGN PATENT DOCUMENTS

WO      WO 99/20303 A    4/1999

OTHER PUBLICATIONS

Innes et al. Annal. N.Y. Acad. Sci. 916: 93-101, 2000.*
Innes et al. Trends in Parasitology 18: 497-504, Nov. 2002.*
Stenlund et al. Parasitol. Res. 83: 214-219, 1997.*

Atkinson, R, et al; "Progress in the Serodiagnosis of *Neospora caninum* Infections of Cattle"; Parasitology Today; 16(3); (2000); pp. 110-114.

Bjorkman, C. et al; "Serological diagnosis of *Neospora caninum* infection"; International Journal for Parasitology; 29 (1999); pp. 1497-1507.

Ellis, J.T. et al; "Development of a single tube nested polymerase chain reaction assay for the detection of *Neospora caninum* DNA"; International Journal for Parasitology; 29 (1999); pp. 1589-1596.

Atkinson, R., et al.; "Comparison of the Biological Characteristics of Two Isolates of *Neospora caninum*"; Parasitology; vol. 118; pp. 363-370 (1999) SP009039632.

Schares, G., et al; "*Neospora caninum*: Identification of 19-, 38-, and 40-kDa Surface Antigens and a 33-kDa Dense Granule Antigen Using Monoclonal Antibodies"; Experimental Parasitology; vol. 92; pp. 109-119 (1999) XP-002304711.

Baszler, T.V., et al; "Detection by PCR of *Neospora caninum* in Fetal Tissues from Spontaneous Bovine Abortions"; Journal of Clinical Microbiology; vol. 37, No. 12; pp. 4059-4064; (1999) XP-002304712.

Schares, G., et al; "Bovine Neosporosis: Comparison of Serological Methods Using Outbreak Sera from a Dairy Herd in New Zealand"; International Journal for Parasitology; vol. 29; pp. 1659-1667; (1999) XP-002304713.

European Examiner's Report (EPO Form 2001); Application No. 01 955 123.3—2403; Mar. 16, 2005, 5 pgs.

Romero, J.J., et al; "Effect of a killed whole *Neospora caninum* Tachyzoite vaccine on the crude abortion rate of Costa Rican dairy cows under field conditions"; Veterinary Parasitology; vol. 123, pp. 149-159 (2004).

Ellis, J.T., et al; "*Hammondia heydorni* oocysts in the faeces of a greyhound"; New Zealand Veterinary Journal; vol. 51, No. 1, pp. 38-39; (2003).

Innes, E.A., et al; "Protection against vertical transmission in bovine neosporosis"; Int'l Journal for Parasiloloty; vol. 31; pp. 1523-1534 (2001).

Quinn, H.E., et al; "*Neospora caninum*: a cause of immune-mediated failure of pregnancy?"; TRENDS in Parasiloloty; vol. 18, No. 9; pp. 391-394 (2002).

Williams, D.J.L., et al; "First demonstration of protective immunity against feotopthy in cattle with latent *Neospora caninum* infection"; Int'l Journal for Parasitology; vol. 33; pp. 1059-1065 (2003).

Guy et al; "Vaccination against *Neospora*-associated abortion in cattle"; Abstract published in Vet. Res; 1 pg (2005).

(Continued)

Primary Examiner—S. Devi
(74) Attorney, Agent, or Firm—Nixon & Vanderhye (57) ABSTRACT

The present invention relates to a novel *Neospora caninum* isolate from Nowra and extracts thereof. The strain is useful in the development of diagnostic assays for the detection of parasites in animals. The present invention also relates to pharmaceutical compositions, using live or killed organisms or extracts thereof, for the treatment and prevention of parasitic infections in animals.

8 Claims, 1 Drawing Sheet

OTHER PUBLICATIONS

Guy, C., et al; "First Draft—Vaccination using viable tachyzoites of *Neospora caninum* protects against foetopathic challenge in pregnant cattle"; *Liverpool School of Tropical Medicine and Division of Livestock Health and Welfare, Faculty of Veterinary Science, Liverpool University*; Liverpool, Merseyside, England; (19 pgs), unpublished now.

Miller, C., et al; "Reduction in transplacental transmission of *Neospora caninum* in outbred mice by vaccination"; *Int'l Journal of Parisitology*; vol. 35; pp. 821-828 (2005).

Jenkins, M.C., et al; "Item 32: Abstracts for references regarding vaccines comprising killed isolates"; (2 pgs), 2003-2004.

Klein, F.; "*Neospora* & Co.: Epidemiology, risk assessments, economics and control"; COST 854—Working group 4 meeting Preceedings; pp. 24-31.

Hall, C.A., et al; "*Neospora* abortion in dairy cattle: diagnosis, mode of transmission and control"; *In Press Veterinary Parasitology*; pp. 1-30.

Guy, C.S., et al; "Vaccination against *Neospora* associated abortion in cattle"; *Veterinary Parasitiology*, University of Liverpool, University of Technology, Sydney, Australia (16 pgs).

Jenkins, M.C., et al; "Evaluation of vaccination with *Neospora caninum* protein for prevention of fetal loss associated with experimentally induced neosporosis in sheep"; *AJVR*, vol. 65, No. 10; pp. 1404-1408 (2004).

Dubey, J.P., et al; "Induced transplacental transmission of *Neospora caninum* in cattle"; *JAVMA*, vol. 201, No. 5; pp. 709-713 (1992).

Lindsay, D.S., et al; Abortions, fetal death, and stillbirths in pregnant pygmy goats inoculated with tachyzoites of *Neospora caninum; Am. J. Vet. Res*, vol. 56, No. 9; pp. 1176-1180 (1995).

Barber, J.S., et al; Characterization of the first European isolate of *Neospora caninum* (Dubey, Carpenter, Speer, Topper and Uggla); *Parasitology*, vol. 111, pp. 563-568 (1995).

Barr, B.C., et al; "Experimental reproduction of bovine fetal *Neospora* infection and death with a bovine *Neospora* isolate"; *J. Vet. Diagn. Invest.*; vol. 6, pp. 207-215 (1994).

Liddell, S., et al; "Prevention of Vertical Transfer of *Neospora caninum* in BALB/c Mice by Vaccination"; *J. Parasitol.*; vol. 85, No. 6; pp. 1072-1075 (1999).

O'Handley, R.M., et al; Vaccination of ewes for prevention of vertical transmission of *Neospora caninum; AJVR*, vol. 64, No. 4, pp. 449-452 (2003).

Ellis, J.T., "Polymerase chain reaction approaches for the detection of *Neospora caninum* and *Toxoplasma gondii*"; *International Journal for Parasitology*; 28 (1998) pp. 1053-1060.

Payne, S., et al; "Detection of *Neospora caninum* DNA by the polymerase chain reaction"; *International Journal for Parasitology*; vol. 26, No. 4, pp. 347-351.

* cited by examiner

NEOSPORA CANINUM ISOLATE

FIELD OF THE INVENTION

The present invention relates to a novel parasitic protozoan isolate and extracts thereof. The strain is useful in the development of diagnostic assays for the detection of parasites in animals. The present invention also relates to pharmaceutical compositions, using live organisms or extracts thereof, for the treatment and prevention of parasitic infections in animals.

BACKGROUND OF THE INVENTION

The Apicomplexa is a diverse phylum of protozoa containing some of the most pathogenic organisms known to man. Representatives include taxa of the well known genera such as *Plasmodium, Babesia* and *Toxoplasma*. In 1984 a research group in Norway reported a previously unknown cyst-forming protozoan which caused encephalitis and myositis in dogs (Bjerkas et al. 1984). These clinical signs were consistent with those caused by *Toxoplasma gondii*, a widely distributed member of the Apicomplexa. However, unlike *T. gondii*, the organism was not pathogenic to outbred mice, nor were *T. gondii* specific antibodies present in the sera of the dogs studied. This prompted further investigation which demonstrated conclusively the organism was ultrastructurally and antigenically distinct from *T. gondii* (Dubey et al 1988). *Neospora caninum* was thus described as a new member of the Sarcocystidae. Soon after, *N. caninum* was implicated as a cause of abortion in cattle (Thilstead & Dubey, 1989).

An increasing number of *N. caninum* isolates have now been obtained, using techniques involving predominantly the direct inoculation of infected tissues onto tissue culture cells (Dubey et al. 1988, Conrad et al. 1993), although bovine isolates have proven difficult to obtain. The primary reason for this has been the detrimental effects of autolysis on the viability of *N. caninum* in aborted bovine fetal tissues. The isolation of a parasite population from a live animal is therefore preferred.

Recent studies on the biological properties of bovine and canine isolates have suggested they belong to a single species called *N. caninum* (Holmdahl et al. 1997), despite the record that wide differences exist between isolates in their biological properties. These include differences in antigenicity, ultrastructure, pathogenicity and genetic heterogeneity (Conrad et al. 1993, Marsh et al. 1995, Lindsay et al. 1995 and Atkinson et al. 1999). Thus not all isolates of *N. caninum* may possess the same properties, and indeed at least one isolate of *N. caninum* was mistakenly identified as *Hammondia heydorni* previously (Schares et al. 2001). Indeed, others have speculated on whether *N. caninum* and *H. heydorni* are the same or different species (Mehlhorn and Heydorn, 2000). *Hammondia heydorni* is also a cyst-forming coccidian that has a life cycle which is very similar to that of *N. caninum*. Thus the true identity of the species *N. caninum* is currently being debated, and its relationship to *H. heydorni* is unclear.

In cattle, abortion due to *N. caninum* infections usually occur in mid- to late gestation, although not all infected foetuses are aborted. Many congenitally infected calves are born healthy and persistently infected, although some infected calves are diseased at birth and die in the neonatal period with lesions similar to those of aborted calves.

The development and use of serological tests for the diagnosis of neosporosis in livestock, along with the identification of animals infected or exposed to *N. caninum*, has been reviewed previously in great detail (Bjorkman et al. 1999; Atkinson et al. 2000a). Significantly, however, there is no effective vaccine against transplacental transmission or foetal loss which occurs as a result of neosporosis and attempts to formulate a vaccine have met with limited success.

Liddel et al. (1999) injected female BALB/c mice with a crude *N. caninum* tachyzoite lysate preparation co-administered with ImmuMAXSR™ adjuvant. These mice were subsequently mated, and pregnant dams were challenged with *N. caninum* tachyzoites at 10-12 days of gestation. Results showed a single injection offered complete protection against transplacental transmission of the parasite to the pups. All pups in this experimental group were free from parasitic infection. No results have yet been reported on the efficacy of this vaccine formulation in the bovine.

Baszler et al. (2000) examined the possibility of vaccination of BALB/c mice with soluble *N. caninum* antigen formulated in either nonionic surfactant vesicles or Freunds Complete Adjuvant. This approach resulted in exacerbation of encephalitis and neurological disease in these mice. These observations were characterised by increased antigen specific IL-4 secretion and increased IgG1:IgG2a ratios in vivo.

Adrianarivo et al. (1999) tested four different adjuvants with a killed whole *N. caninum* tachyzoite preparation for immunogenicity. The results indicated that the immune responses, as determined by IFAT titres, were significantly higher in experimentally infected cattle compared to immunised cattle.

Adrianarivo et al. (2000) studied the effect of a killed *N. caninum* tachyzoite preparation in pregnant cattle using a POLYGEN™ adjuvant. Heifers were injected at day 35 and day 65 of gestation and four weeks later were challenged with intravenous or intramuscular injection of tachyzoites. Post immunisation, heifers developed both humoral and cell mediated immune responses characterised by an increase in production of IgG1 and IFN-γ respectively. Following a challenge with *N. caninum* tachyzoites, however, significant cell mediated immune response did not occur. All foetuses in the study, both from control and experimental cattle, developed lesions characteristic of *N. caninum* infection. Failure to prevent foetal infection by this formulation in pregnant cattle was concluded.

Unlike the development of killed or genetically engineered vaccines against parasites, vaccines based on live populations of parasites are available, for example against Toxoplasma-induced abortion in sheep (Buxton & Innes, 1995) and Eimeria parasites of poultry (Shirley & Bedrnik, 1997). A live vaccine is not, however, available against *N. caninum*.

The literature on live vaccines against *N. caninum* is limited. Atkinson et al. (1999) showed that infection of naive mice by the Nc-SweB1 isolate of *N. caninum* partially protected them against a severe infection by Nc-Liverpool. Lindsay et al. (1999) generated temperature sensitive mutants of *N. caninum* and demonstrated that they could prevent clinical signs associated with neosporosis in mice.

SUMMARY OF INVENTION

The present inventors have isolated a novel protozoan parasite from the central nervous system of a dairy calf. The parasite was identified based on a number of criteria as an isolate of *Neospora caninum* and was called the "Nc-Nowra" strain. This isolate is naturally attenuated in its ability to cause neosporosis in a laboratory animal, and thus is an ideal isolate to serve as a basis for a vaccine against this disease.

A sample of the Nc-Nowra isolate was deposited under the provisions of the Budapest Treaty on Jun. 21, 2001 with the Australian Government Analytical Laboratories (AGAL) and accorded AGAL Accession No NM01/22338. Further, a sample of Vero cells was deposited under the provisions of the Budapest Treaty on Jun. 21, 2001 with the Australian Government Analytical Laboratories (AGAL) and accorded AGAL Accession No NM01/22339.

Accordingly, in a first aspect the present invention provides a parasitic protozoan isolate having the characteristics of the isolate deposited as AGAL Accession No. NM01/22338.

In a preferred embodiment of the first aspect, the isolate is that deposited as AGAL Accession No. NM01/22338.

In a second aspect, the present invention provides an antibody raised against an isolate according to the first aspect. Preferably, the antibody is a monoclonal antibody.

In a third aspect the present invention provides a host cell infected with an isolate of the first aspect. Preferably, the host cell is derived from the sample deposited as AGAL Accession No NM01/22339.

In a fourth aspect, the invention provides a vaccine composition comprising an isolate of the first aspect, wherein the isolate is in the form of a lolled parasite population or live attenuated parasites.

The present invention also provides a vaccine composition comprising an extract or an isolate according to the first aspect. Preferably, the extract is selected from the group consisting of live attenuated, killed and fixed parasites, a cell lysate, an antigenic polypeptide and a polynucleotide encoding an antigenic polypeptide.

In a fifth aspect, the present invention provides a method for the treatment or prevention of infection or disease in an animal, the method comprising administering to the animal a vaccine composition according to the fourth aspect.

In a sixth aspect, the present invention provides a method for the treatment or prevention of infection or disease in an animal, the method comprising administering to the animal an antibody according to the second aspect.

In a seventh aspect, the present invention provides a method of diagnosing a parasitic infection or disease in an animal, the method comprising identifying the presence of the isolate according to the first aspect of the invention.

In a preferred embodiment of the fifth, sixth or seventh aspects, the parasitic disease is neosporosis. In a further preferred embodiment the parasitic infection is due to the presence of *Neospora caninum*. In one embodiment the *Neospora caninum* is the isolate of the first aspect.

DETAILED DESCRIPTION OF THE INVENTION

The parasitic isolate of the present invention may be used to develop diagnostic tools or aids for the detection or diagnosis of parasitic disease in animals. Such diagnostic tools or aids include antigenic polypeptides derived from the isolate, antibodies raised against the isolate and molecular probes or primers derived from the genome of the isolate.

Standard protein purification techniques can be used to isolate antigenic polypeptides from the novel parasitic strain of the present invention. Such techniques include selective precipitation with such substances as ammonium sulphate, column chromatography, immunopurification methods, and the like. See, for instance, R. Scopes, Protein Purification: Principles and Practice, Springer-Verlag: New York (1982). Proteins and portions thereof isolated from the strain can be sequenced according to standard techniques as described for instance in Sambrook et al., Molecular Cloning, A Laboratory Manual, Cold Spring Harbour Publish., Cold Spring Harbour, N.Y. 2nd Ed (1989).

Antibodies raised against the strain may be polyclonal or monoclonal antibodies.

If polyclonal antibodies are desired, a selected mammal (e.g., mouse, rabbit, goat, horse, etc.) may be immunised with an immunogen preferably a purified protein mixed with an adjuvant. Serum from the immunised animal is collected and treated according to known procedures. Further fractionation of the antisera to enrich for antibodies reactive to the isolated proteins of the invention can be done if desired.

Monoclonal antibodies may be obtained by various techniques by one skilled in the art Briefly, spleen cells in an animal immunised with a desired immunogen are immortalised, commonly by fusion with a myeloma cell (See, Koller & Milstein, Eur. J. Immunol. 6:511-519 (1976)). Alternative methods of immortalization include transformation with Epstein Barr Virus, oncogenes, or retroviruses, or other methods well known in the art. Colonies arising from single immortalised cells are screened for production of antibodies of the desired specificity and affinity for the desired antigen.

Antibodies, both monoclonal and polyclonal, which are directed against epitopes are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the antigen of the agent against which protection is desired.

Techniques for raising anti-idiotype antibodies are known in the art. These anti-idiotype antibodies may also be useful in therapy.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv).

In one embodiment, the antibodies of the present invention bind specifically to the Neospora isolate of the present invention.

Antibodies of the invention may be bound to a solid support and/or packaged into kits in a suitable container along with suitable reagents, controls, instructions and the like.

Molecular probes or primers for detecting the isolate of the present invention may be generated by recombinant or synthetic means. Preferably, the polynucleotide is at least 16 nucleotides in length, more preferably at least 20, 25, 30 or 40 nucleotides in length. The polynucleotide may be used to produce a primer, e.g. a PCR primer, a primer for an alternative amplification reaction, or a probe e.g. conjugated by conventional means to a radioactive or non-radioactive label.

Diagnosis may be achieved by detecting the presence of the parasite or by assaying for antibodies to the parasite in the animal. As there is now concern that humans are susceptible to these type of parasite infections, the present invention includes human applications.

The parasite may be detected by culturing the parasite from a clinical specimen and identifying the parasite by microscopy, or may be identified by the use of antibodies to the parasite or by detecting a portion of the genome of the parasite by molecular biological techniques. The clinical specimen may be a biopsy, stool specimen, blood sample, foetal tissue or the like. It will be appreciated that the discovery of the parasite and its association with parasitic disease will allow its detection by any of the known methods of the art. It will also be appreciated that molecular detection methods like polymerase chain reaction (PCR) can also be used to identify the presence of the parasite in a clinical specimen.

Immunological and immunoassay procedures in general, are described in Basic And Clinical Immunology 7th Ed. (D. Stites and A. Terr ed.) 1991. According to the present invention immunoassays may by performed in any of several configurations, which are reviewed extensively in Enzyme Immunoassay, E. T. Maggio, ed., CRC Press, Boca Raton, Fla. (1980); Practice and Theory of Enzyme Immunoassays," P. Tijssen, Laboratory Techniques In Biochemistry And Molecular Biology, Elsevier Science Publishers B. V. Amsterdam (1985). For example, a person skilled in the art would understand that the proteins and antibodies according to the present invention can be used in ELISA, immunoblot analysis and agglutination assays.

In brief, immunoassays to measure antibodies or antigens are either competitive or noncompetitive binding assays. In competitive binding assays, the sample analyte (e.g., anti-*N. caninum* antibodies) competes with a labelled analyte (e.g., anti-*N. caninum* monoclonal antibody) for specific binding sites on a capture agent (e.g., isolated *N. caninum* protein) bound to a solid surface. The concentration of labelled analyte bound to the capture agent is inversely proportional to the amount of free analyte present in the sample.

Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means.

Alternatively, the immunoassay is carried out in liquid phase and a variety of separation methods are employed to separate the bound labelled component from the unbound labelled components. These methods are known to those skilled in the art and include, but are not limited to, immunoprecipitation, column chromatography, adsorption, addition of magnetisable particles coated with a binding agent and other similar procedures.

In another alternate procedure, an immunoassay is carried out in liquid phase without a separation procedure. Typically, in these procedures, the assayed protein or other analyte competes with a compound for binding to an antibody attached to a label. The binding of the analyte to an antibody, but not the binding of the compound to the antibody, causes a change in the signal emitted by the label, so that analyte binding is measured without separating the bound from the unbound labelled component.

Western blot (immunoblot) analysis is also used to detect the presence of antibodies to the parasitic isolate in a biological sample. This technique is a reliable method for confirming the presence of antibodies against a particular protein in the sample.

Pharmaceutical compositions prepared using extracts of the isolate of the present invention may be used for the treatment and/or prevention of parasitic infections, preferably *N. caninum* infections.

Preferably, the extract is selected from the group consisting of live attenuated parasites, killed and fixed parasites, cell lysates, antigenic polypeptides and polynucleotides encoding antigenic polypeptides.

Vaccines of the invention may comprise a crude extract of the novel parasitic isolate. Killed and/or chemically fixed parasites or cells can also be used. Vaccines may also comprise partially or completely purified polypeptide preparations derived from the parasitic isolate. The polypeptide may be an antigen produced by recombinant DNA technology.

In addition, polynucleotide sequences derived from the novel parasitic isolate may be cloned into viruses that transfect host cells in animals. Live attenuated viruses, such as vaccinia or adenovirus, are convenient alternatives to vaccines because they are inexpensive to produce and are easily transported and administered. It will be appreciated that polynucleotides derived from the parasitic isolate of the present invention may also be incorporated into non-viral vaccine vectors.

The preparation of vaccines which contain an immunogenic polypeptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis,* polyribonucleotides, sodium alginate, lanolin, lysolecithin, vitamin A, saponin, liposome, levamisole, DEAE-dextran, blocked copolymers or other synthetic adjuvants. Such adjuvants are available commercially from various sources, for example, Freund's Incomplete Adjuvant and Complete Adjuvant (Difco Laboratories, Detroit, Mich.).

Typically, adjuvants such as Quil A, AMPHIGEN™, ALHYDROLGEL™, or a mixture of AMPHIGEN™ and ALHYDROGEL™ are used. Other immunostimulatory molecules such as cytokines (for example, γ-interferon) may also be used.

The proportion of immunogen and adjuvant can be varied over a broad range so long as both are present in effective amounts. For example, aluminum hydroxide can be present in an amount of about 0.5% of the vaccine mixture ($Al_2O_3$ basis). Conveniently, the vaccines are formulated to contain a final concentration of immunogen in the range of from 0.2 to 200 µg/ml, preferably 5 to 50 µg/Ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Vaccine compositions of the present invention may be administered to animals susceptible to or otherwise at risk of infection to elicit an immune response against the parasite and thus enhance the animals own immune response capabilities. Such an amount is defined to be an "immunogenically effective amount". In this use, the precise amount depends on the judgement of the prescribing veterinarian or doctor and would include consideration of the patient's state of health and weight, the mode of administration, the nature of the formulation, and the like.

A variety of vaccination regimes may be effective in immunising cattle and other animals. Preferably, female cattle are vaccinated just prior to or at the time of breeding so as to prevent abortion and reduce the possibility of congenital infections. A second immunisation may be given at other time periods before and during gestation. Calves and adult males may also be vaccinated, if desired. Animals that have previously been exposed to *N. caninum* or have received colostral antibodies from the mother may require booster injections. The booster injection is preferably timed to coincide with times of maximal challenge and/or risk of abortion.

In order that the present invention may be more clearly understood preferred forms will be described with reference to the following examples and drawings.

EXAMPLE 1

Isolation of Bovine *Neospora* sp. in New South Wales

The isolation and characterisation of a Neospora parasite from a clinically normal neonatal Australian Holstein-Friesian calf is described. The calf was born from a dam maintained in a commercial dairy herd of Holstein-Friesian cattle located on the south coast of New South Wales (NSW) Australia, near Nowra. This herd has been endemically infected with neosporosis for a number of years and has been studied extensively (Atkinson et al. 2000b). The dam was first identified as being serologically positive with an IFAT titre of 1280 for *N. caninum* in March 1995, having previously aborted in January 1994 but not since. The calf, which was seropositive to *N. caninum* antigen by western blotting, remained healthy and showed no clinical signs of *N. caninum* infection prior to it's euthanasia (NSW Agriculture) with intravenous potentiated pentabarbitone (EU-THETAL™) via jugular puncture with a 21 gauge needle and 20 ml syringe, dosed to effect. On cessation of life, the brain and spinal cord (including thoracic segments T10 to T15) were removed following dissection of the tissues of the skull and cervical region and exposure of the central nervous system (CNS) using a saw and bone cutters. With the exception of a 3 cm diameter segment of left frontal cerebral cortex which was fixed in 10% formalin for histological processing, the CNS tissues were placed immediately in antibiotic saline solution (0.9% NaCl containing penicillin and streptomycin) and homogenised. Trypsin was then added to 0.05% and the homogenate incubated for 30 mm at 37° C. The homogenate was centrifuged for 10 mm at 1200 g and resuspended in antibiotic saline. The pellet was washed twice in antibiotic saline with centrifugation.

For tissue culture, the pellet was resuspended in 8 ml of tissue culture medium and placed using aseptic technique into a flask containing a monolayer of vero cells (Barber et al. 1995). Unfortunately the cultures became contaminated and were discarded.

Homogenates in antibiotic saline were injected intraperitoneally into interferon-gamma receptor knockout (IFN-γRKO, 129/Sv) mice with a 23 gauge needle. Mice were injected with homogenate from either infected brain (6 mice) or spinal cord extract (6 mice) and then monitored daily for clinical signs of disease. Clinical signs suggestive of neosporosis including ruffled coat, huddled lethargic appearance and weight loss (Atkinson et al. 1999), were observed in both groups of mice (brain and spinal cord injected) within 23 days post-inoculation with homogenate. Mice were euthanased with carbon dioxide and their brains removed and processed as above for infection of tissue culture cells with bovine brain tissue, however using smaller volumes. Brain homogenates were also passaged back into naive IFN-γRKO knock-out mice, which developed clinical signs of neosporosis by 23 days post infection. A third passage in mice resulted in clinical signs being observed from 10 days post infection.

Histopathological examinations, performed by NSW Agriculture, of multiple sections of cerebrum from the clinically normal calf identified very mild multifocal non-suppurative encephalitis characterised by rare foci of gliosis and perivascular cuffing. No parasitic elements were observed, however, the lesions were considered consistent with very mild intrauterine cerebral infection with *N. caninum* (Boulton et al. 1995). Histological examination of cerebrum from 5 mice inoculated with calf brain homogenates identified mild multifocal non-suppurative encephalitis in all 5, with 2 apicomplexan structures resembling *N. caninum* tachyzoites identified in the cerebral choriod tissue section of a single mouse. Immunohistochemistry performed on this section identified positive immunoperoxidase staining with anti-Neospora antisera.

Vero cells infected with brain homogenate from one of these mice resulted in the proliferation of tachyzoites 14 days post infection. The in vitro growth of these parasites has now been successfully achieved for 15 months. The isolate was identified as a member of the genus Neospora for the reasons outlined below and was named Nc-Nowra, after the geographical location of the study herd.

EXAMPLE 2

Characterisation of Isolated Organisms

Electron microscopy. Tachyzoites were recovered from in vitro culture and examined by transmission electron microscopy. Tachyzoites were fixed in 2.5% glutaraldehyde, 2% paraformaldehyde in phosphate buffer pH 7.2 for 2 hrs; washed three times with 0.1M cacodylate buffer and post-fixed in 1% aqueous osmium tetroxide. After excess fixative was removed by washing with water, parasites were dehydrated in ethanol, transferred to anhydrous acetone and infiltrated and embedded in Epon resin. The blocks were cut and ultrathin sections examined with a JEM 1010 transmission electron microscope. Tachyzoites were identified as *N. caninum* by virtue of their size, shape and internal structures including the presence of characteristic intracellular organelles such as electron dense rhoptries (Speer et al. 1999).

Western blotting. Tachyzoite lysates of Nc-Nowra, Nc-Liverpool and the ME49 strain of *T. gondii* were analysed by western blotting using sera obtained from mice acutely infected with Nc-Liverpool (Atkinson et al. 1999). The antigen profile detected for Nc-Nowra was similar, but not identical to, that obtained from Nc-Liverpool. The antigen profile possessed no similarity to that shown by *T. gondii*.

PCR and DNA sequencing. PCR amplification of Nc-Nowra genomic DNA was performed using DNA prepared by standard techniques, from in-vitro cultured tachyzoites. The primers Tim3 and Tim11 were used and the amplification products were analysed by agarose gel electrophoresis (Payne and Ellis, 1996). PCR specifically amplified an internal transcribed spacer (ITS1) sequence, which was similar in size to that obtained from Nc-Liverpool DNA. The PCR product was purified using a QIAGEN™ purification kit and the DNA sequenced by cycle sequencing using primers Tim3 and Tim11. A consensus sequence derived for the ITS1 of Nc-Nowra was 99% similar to that previously reported for *N. caninum* (AF029702 and AF038860 for example).

EXAMPLE 3

Nc-Nowra Tachyzoites Used in a Serological Test such as an ELISA

A dairy herd, located in the Southern Highlands of NSW, contained 177 Friesians with a history of abortion, with 37 abortions being recorded over 18 months spanning 1999/2000. There were two dogs and numerous foxes on this property, and *N. caninum* was previously diagnosed on the property by post mortem examination of aborted foetuses by NSW Agriculture. The herd is regularly and fully vaccinated against leptosporidiosis. The dairy herd was bleed for routine investigation of the cause of the abortions and these sera were screened for antibodies to Nc-Nowra using an indirect ELISA protocol developed at UTS and described below.

Nc-Nowra tachyzoites were recovered from in vitro culture and reduced to protein extracts by resuspension in lysis buffer (20 mM Tris pH 7.5, 150 mM NaCl, 1% TRITON™ X-100, 1 mM PMSF, 2 mM DTT, 1 mM benzimidine HCl) and disruption by sonication at 50W/20 KHz for 10-20 secs. The resulting preparation was dialysed against PBS overnight at 4° C. with one change of buffer. Protein concentration was determined using the Bradford dye-binding assay (Biorad). NUNC™ 96 well plates were coated with antigen diluted to 1 µg/well in carbonate buffer at 4°C. overnight. Plates were washed three times with PBS/0.03% TWEEN™, and the test bovine serum diluted in ELISA buffer 2 (0.3% TWEEN™, 0.05% bovine haemoglobin) was added to wells. The sera used were from dairy cattle which were prone to abortion. Plates were again incubated overnight at 4° C. and then washed three times with PBS/0.03% TWEEN™. Anti-bovine IgG-alkaline phosphatase conjugate was diluted 1:6,000 in buffer 2 and plates were incubated at 37° C. for 3 hrs. Plates were washed with PBS/0.03% TWEEN™ and 1 mg/ml of p-nitrophenylphosphate in carbonate buffer was added. Plates were incubated at 37° C. for 3 min and absorbance at 405 nm read in a Biorad ELISA plate reader. A positive serum was identified as being 2 standard deviations greater than the mean negative O.D. result (from 20 sera).

Figure 1:
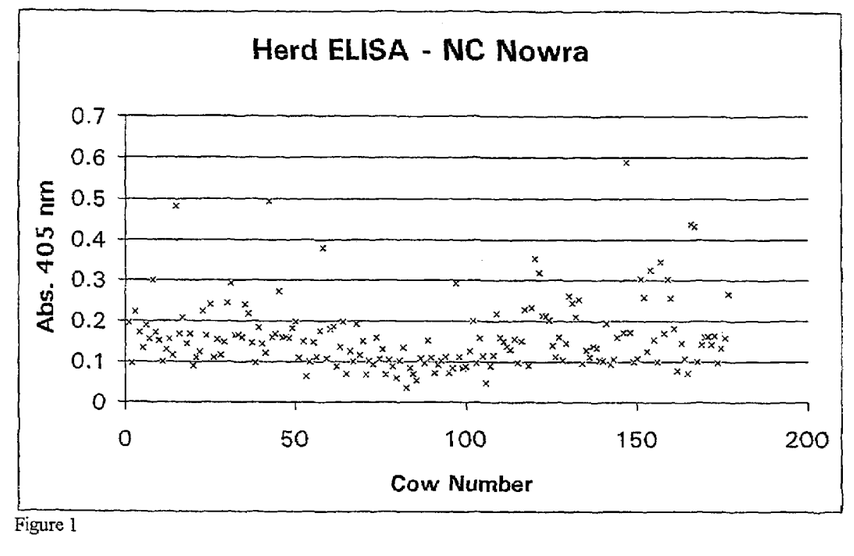
FIG. 1. Scatterplot showing sera ELISA readings against *N. caninum* for individual cows of the study herd.

Results. Nc-Nowra crude lysate was used in an ELISA to screen a dairy herd suspected of containing *N. caninum* positive cows. A graph showing a summary of the O.D. readings obtained from the herd ELISA is in FIG. 1. Four (4) of 177 (2.3%) cows in the herd were seropositive to *N. caninum* using this assay. There was a high correlation between ELISA absorbances obtained using the Nc-Nowra ELISA and the results from a commercial *N. caninum* ELISA kit, which detected 16 of 177 (9%) cows as seropositive within the herd. The commercial kit is also based on a crude lysate antigen, however the NC-1 *N. caninum* isolate is used. This was isolated in the U.S.A. and has different biological properties to the Nc-Nowra isolate.

EXAMPLE 4

A Cell Extract of Nc-Nowra Used to Induce an Immune Response in an Animal

Thirty (30) QS mice were divided equally into 10 groups, each of which received one of the following treatments, 4 weeks apart:

| GROUP | TREATMENT |
|---|---|
| 1. | None |
| 2. | Freund's incomplete adjuvant (FIA) alone |
| 3. | FIA + Nc-Nowra |

Two (2) weeks after the second injection, mice were killed by $CO_2$ asphyxiation, bled and their spleens removed for a cell proliferation assay.

An Nc-Nowra extract was made in the following way and used for either injection into animals or for ELISA. Nc-Nowra tachyzoites were recovered from in vitro culture and reduced to protein extracts by resuspension in lysis buffer (20 mM Tris pH 7.5, 150 mM NaCl, 1% Triton X-100, 1 mM PMSF, 2 ml DTT, 1 mM benzimidine HCl) and disruption by sonication at 50W/20 Hz for 10-20 secs. The resulting preparation was dialysed against PBS overnight at 4° C. with one change of buffer. Protein concentration was determined using the Bradford dye-binding assay (Biorad).

Sera, made by standard procedures, was assayed by ELISA using the following method. NUNC™ 96 well plates were coated with Nc-nowra antigen extract diluted to 1

μg/well in carbonate buffer at 4° C. overnight. Plates were washed three times with PBS/0.03% TWEEN™ and mouse serum diluted in ELISA buffer 2 (0.3% TWEEN™, 0.05% bovine haemoglobin) was added to wells. Serum used was from mice in the treatment groups as described above. Plates were again incubated overnight at 4° C. and then washed three times with PBS/0.03% TWEEN™. Anti-mouse IgG-alkaline phosphatase conjugate was diluted 1:6,000 in buffer 2 and plates were incubated at 37° C. for 3 hrs. Plates were washed with PBS/0.03% TWEEN™ and 1 mg/ml of p-nitrophenyiphosphate in carbonate buffer was added. Plates were incubated at 37° C. for 30 mm and absorbance at 405 nm read in a Biorad ELISA plate reader.

Cell proliferation assays were performed on mouse spleen cells as follows. Spleens were individually placed in wash medium (DMEM containing penicillin and streptomycin, DMEM(PS), and forced through a 70 μm nylon disposable sieve to yield a single cell suspension. The cells were concentrated by centrifugation and resuspended in 2 mls red cell lysis buffer and left at room temp. for 1 min. The lysis buffer was diluted out with more DMEM/PS, centrifuged and the pellets resuspended in fresh DMEM/PS for counting. $1 \times 10^4$ cells per well of each suspension were added in triplicate to wells of a microtitre plate. Stimulating antigen at a concentration of 10 μg/well for Con A and Nc-Nowra lysate was added to the cells. A blank (containing no cells) was included. The cells were incubated at 37° C. in 5% $CO_2$ for 4 days. BrdU was then added and the cells incubated for a further 4 hours. The cells were pelleted to the bottom of the microtitre plate by centrifugation, the supernatants collected for cytokine assay, and the cells dried and fixed. BrdU incorporation was then detected using a commercial immunoassay kit (Roche) encompassing an anti-BrdU-POD conjugate.

Results. An increase in absorbance was observed in the serum samples taken at each time point indicating an IgG response was raised in mice against a crude antigen extract of Nc-Nowra. This response was significantly greater than that seen in uninjected mice or mice injected with adjuvant alone. The time course showed a significant IgG response at and after 6 weeks post injection in the mice receiving Nc-Nowra extract.

A crude extract of Nc-Nowra, when used as a stimulating antigen, also stimulated cell proliferation in spleen cells from mice, showing a cell mediated immune response was induced.

EXAMPLE 5

Nc-Nowra is Only Mildly Pathogenic in the Mouse

A single experiment was performed to investigate the pathogenicity of Nc-Nowra in the BALB/C mouse. This model has been used previously to investigate the pathogenicity of *N. caninum* (Nc-Liverpool and Nc-SweB1) in vivo (Atkinson et al. 1999). Groups of female mice were injected intraperitoneally with either saline, $10^6$ (Nc-Liverpool or Nc-Nowra) or $10^4$ (Nc-Nowra) tachyzoites grown in-vitro. Mice were weighed daily and euthanased when clinical signs dictated (to alleviate unnecessary suffering) or at the end of the experiment at day 31 post-infection. The brains of all mice in the experiment were removed, fixed in 10% formalin and examined pathologically.

Results. All mice injected with saline survived until the end of the experiment and gained weight steadily over this time period. Mice given Nc-Liverpool rapidly became ruffled and lethargic and euthanasia of affected mice began at day 20 post infection. By day 31, only 4 out of 9 mice remained in this group. Mice given Nc-Nowra were not as rapidly affected with 7 out of 17 mice surviving until day 31 post infection.

Histological sections from 3 of the mice injected with saline failed to identify significant histological lesions (no further mice were examined in this group). Lesions of varying severity and characterised as multifocal non-suppurative to necrotising encephalitis were identified in 5 of 8 mice receiving $10^4$ Nc-Nowra, all of 9 mice receiving $10^6$ Nc-Nowra and all of 9 mice receiving $10^6$ Nc-Liverpool. Lesions were graded in severity as per previous studies (Atkinson et al. 1999) with 4 of the mice receiving $10^4$ Nc-Nowra, 4 of the mice receiving $10^6$ Nc-Nowra and all 9 mice of the $10^6$ Nc-Liverpool mice, judged to have moderate to severe lesions. These findings show that, like Nc-SweB1, which was also isolated from the bovine (Stenlund et al. 1997), Nc-Nowra is less pathogenic in the BALB/C mouse, compared to Nc-Liverpool.

Five (5) BALB/C mice injected i.p. with Nc-Nowra infected brain from a knock-out mouse were maintained in a healthy condition for 7 months, and showed no clinical signs of neosporosis. These mice seroconverted to *N. caninum* antigen (by western blotting). After euthanasia, analysis of brain pathology showed mild brain lesions consistent with *N. caninum* infection. No parasitic stages were seen during the pathologic analyses.

EXAMPLE 6

A Live Infection by Nc-Nowra can Prevent Neosporosis in Mice Infected with Nc-Liverpool Tachyzoites of the Nc-Nowra isolate were harvested from an in vitro culture of Vero cells and diluted in 0.9% saline to a concentration of $10^5$/ml. Ten BALB/c mice were infected subcutaneously with $10^4$ tachyzoites per mouse. A further fifteen mice were injected with 0.9% saline only. Three weeks post infection the ten Nc-Nowra infected mice and ten of the saline injected mice were infected with $10^6$ Nc-Liverpool tachyzoites recovered from tissue culture. The five remaining saline injected mice were injected with saline again. The mice were monitored daily for clinical signs (ruffled and lethargic) and weighed daily from day 13 p.i. Mice were euthanased after losing 20% of their body weight. Blood was collected from all mice and brains from a selection from each group. The blood was allowed to clot, spun and the serum removed. The brains were fixed in 10% formalin and sent to NSW Agriculture for pathologic examination.

Results

Group 1: injected with saline and challenged with Nc-Liverpool (positive control, n=10):

Clinical signs were observed in the Nc-Liverpool only infected mice on day 14 p.i. and euthanasia of mice started on day 21. All ten mice in this group died between day 21 and day 25 p.i.

Group 2: infected with Nc-Nowra and challenged with Nc-Liverpool (n=10):

In contrast, only 2 mice in the Nc-Nowra/Nc-Liverpool infected mice developed clinical signs and these were euthanased on days 19 and 20. Both of these mice were small and light in weight for their age at the beginning of the experiment. Such mice normally succumb quickly to neosporosis and were included as an internal positive control. All eight other mice in this group remained healthy throughout the experiment and showed no signs normally associated with N. caninum infection such as weight loss, head tilting or motor discoordination. It was concluded that the Nc-Nowra infection had induced protective immunity against the clinical signs of neosporosis associated with Nc-Liverpool infection.

Group 3: injected with saline and given no parasite challenge (negative control, n=5)

All mice in this group remained healthy.

Brain Pathology

Five (5) micron sections were cut from brains, stained with H and E and examined for evidence of brain lesions. Lesions were graded on a scale of 0 to 5 with 5 being the most severe type of lesion. The average score for the Nc-Liverpool infected brains (Group 1) examined was 3.5 while the average score for the Nc-Nowra/Nc-Liverpool (Group 2) infected brains examined was 1.5. It was concluded that the prior Nc-Nowra infection had significantly reduced brain lesion score in this experiment.

EXAMPLE 7

Prior Infection by Nc-Nowra has no Effect on Litter Size in the Pregnant QS Mouse Five (5) week-old, female QS mice were injected subcutaneously with $10^4$ in-vitro derived tachyzoites of Nc-Nowra. Three weeks later ovulation in all mice was synchronised by two hormone injections (PMSG and hCG) given 48 hours apart. At day 8 of pregnancy 1 of the treatment groups was given $10^6$ tachyzoites of Nc-Liverpool. All mice were killed at day 14 of pregnancy and the uterine implantation sites were analysed for viable foetuses.

Results: The table below summarises the treatment groups and the mean litter sizes obtained. No significant difference in mean litter size was found between the treatment groups, indicating Nc-Nowra does not cause foetal loss in this model.

| Treatment | Mean Litter Size (S.E.) | Number of mice in the group |
| --- | --- | --- |
| None | 15.2 (1.18) | 23 |
| Nc-Nowra | 16.9 (1.73) | 12 |
| Nc-Nowra/Nc-Liverpool | 17.3 (1.45) | 19 |

Figure 2:
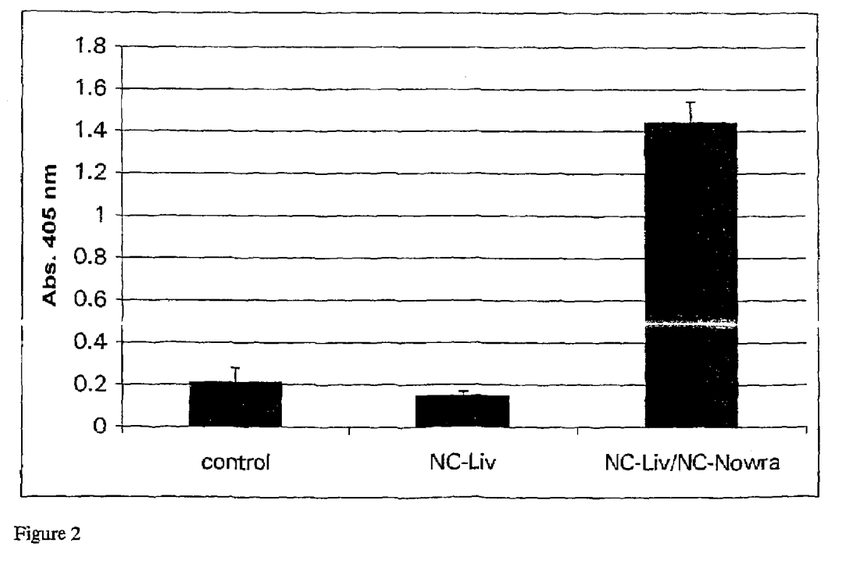
FIG. 2. Bar chart showing IgG responses (as ELISA absorbances) to *N. caninum* antigen in mice infected with or without Nc-Nowra before pregnancy. Groups given Nc-Liverpool at day 8 of pregnancy are indicated. Only mice receiving Nc-Nowra before pregnancy gave high IgG titres.

Sera from all dams killed at day 14 were assayed for IgG to N. caninum antigen using the ELISA method described in Example 4. Mice infected with Nc-Nowra showed high levels of IgG to N. caninum, whereas mice in the other two groups did not (FIG. 2).

EXAMPLE 9

Infection of Pregnant QS Mice with Nc-Nowra

Nine (9) week-old female QS mice were mated following synchronisation of ovulation with 2 hormone injections (PMSG and hCG) 48 hrs apart. At day 8 of gestation mice were given either a subcutaneous injection of saline (control group), $1\times10^4$ or $1\times10^6$ Nc-Nowra tachyzoites derived from tissue culture. All mice were euthanased at day 14 of gestation and uterine implantation sites were analysed for viable and non-viable foetuses. Statistical analyses was performed using an Analysis of Variance.

Total nucleic acid was made from the excised foetal tissue by standard methods involving lysis in buffer containing SDS, EDTA and proteinase K, followed by phenol chloroform extraction and ethanol preciptation. These DNAs were analysed for the presence of N. caninum DNA by PCR using primers that were designed to be specific for N. caninum from the sequence of the ITS1 reported previously (Payne and Elis, 1996). The PCR reaction was heated at 95° C. for 2 min, then subject to 35 cycles of 95° C. 45 sec, 50° C. 45 sec and 72° C. for 2 min. The reaction was then treated at 72° C. for 5 min to allow primer extension to be complete.

Results: The table below summarises the results of this experiment. Injection of mice with Nc-Nowra at day 8 of gestation caused no clinical signs of disease and no significant foetal loss (p=0.3355).

| Group | Mean % of resorptions/litter (S.E.) |
| --- | --- |
| Saline | 6.813 ± 3.535 |
| $1 \times 10^4$ Nc-Nowra | 26.75 ± 24.43 |
| $1 \times 10^8$ Nc-Nowra | 7.243 ± 3.626 |

No N. caninum-specific PCR product was obtained from these foetal DNAs, showing no evidence for N. caninium infection at day 14 of gestation. The positive control (N. caninum DNA) gave the required band of approx. 400 bp. This study does not exclude the possibility that N. caninum may be detected in older foetuses or pups using a similar experimental design with Nc-Nowra.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

REFERENCES

Andrianarivo A G, Choromanski L, McDonough S P, Packham A E & Conrad P A. (1999) Immunogenicity of a killed whole Neospora caninum tachyzoite preparation formulated with different adjuvants. International Journal for Parasitology 29,1913-1625.

Andrianarivo A G, Rowe J D, Barr B C, Anderson M L, Packham A E, Sverlow K W, Choromanski L, Loui C, Grace A & Conrad P A. (2000) A POLYGEN™-aduvanted killed Neospora caninum tachyzoite preparation failed to prevent foetal infection in pregnant cattle following i.v/i.m experimental tachyzoite challenge. International Journal for Parasitology 30, 985-990.

Atkinson R, Harper P A W, Ryce C, Morrison D A & Ellis J T. (1999) Comparison of the biological characteristics of two isolates of *Neospora caninum*. *Parasitology* 118, 363-370.

Atkinson R. Harper P A W, Reichel M P & Ellis J T. (2000a) Progress in the serodiagnosis of *Neospora caninum* infections of cattle. *Parasitology Today* 16,110-114.

Atkinson R A, Cook R W, Reddacliff L, et al. (2000b) Seroprevalence of *Neospora caninum* infection following an abortion outbreak in a New South Wales dairy herd. *Australian Veterinary Journal* 78, 262-266.

Barber J S, Holmdahl O J M, Owen M R et al. (1995) Characterisation of the first European isolate of *Neospora caninum* (Dubey, Carpenter, Speer, Topper and Uggla). *Parasitology* 111, 563-568.

Baszler T V, McElwain T F & Mathison B A. (2000) Immunization of BALB/c mice with killed *Neospora caninum* tachyzoite antigen induces a Type 2 immune response and exacerbates encephalitis and neurological disease. *Clinical and Diagnostic Laboratory Immunology* 7, 893-898.

Bjerkas I, Mohn S F & Presthus J (1984) Unidentified cyst-forming sporozoan causing encephalomyelitis and myositis in dogs. *Zeitschrift fur Parasitenkunde* 70, 271-274.

Bjorkman C & Uggla A. (1999) Serological diagnosis of *Neospora caninum* infection. *International Journal for Parasitology* 29, 1497-1507.

Boulton J G, Gill P A, Cook R W, et al. (1995) Bovine Neospora abortion in north-eastern New South Wales. *Australian Veterinary Journal* 72, 119-120.

Buxton D & Innes E A. (1995) A commercial vaccine for bovine toxoplasmosis. *Parasitology* 110 Suppl: S11-6.

Conrad P A, Barr B C, Sverlow K W, Anderson M, Daft B, Kinde H, Dubey J P, Munson L & Ardans A. (1993). In vitro isolation and characterization of a Neospora sp. from aborted bovine foetuses. *Parasitology* 106, 239-249.

Dubey J P, Carpenter J L, Speer C A, Topper M J & Uggla A. (1988) Newly recognized fatal protozoan disease of dogs. *Journal of the American Veterinary Medicine Association* 192, 1269-1285.

Holmdahl J, Bjorkman C, Stenlund S, Uggla A & Dubey J P. (1997) Bovine Neospora and *Neospora caninum*—one and the same. *Parasitology Today* 13, 40-41.

Liddell S, Jenkins M C, Collica C M & Dubey J P. (1999) Prevention of vertical transfer of *Neospora caninum* in BALB/c mice by vaccination. *Journal of Parasitology* 85, 1072-1075.

Lindsay D S, Lenz S D, Cole R A, Dubey J P & Blagburn B L. (1995) Mouse model for central nervous system *Neospora caninum* infections. *Journal of Parasitology* 81, 313-315.

Lindsay D S, Lenz S D, Blagburn B L & Brake D A (1999) Characterization of temperature-sensitive strains of *Neospora caninum* in mice *Journal of Parasitology* 85, 64-67.

Marsh A E, Barr B C, Sverlow K, Ho M, Dubey J P & Conrad P A. (1995) Sequence analysis and comparison of ribosomal DNA from bovine Neospora to similar coccidial parasites. *Journal of Parasitology* 81, 530-535.

Mehlhorn H & Heydorn A O. (2000) *Neospora caninum:* Is it really different from *Hammondia heydorni* or is it a strain of *Toxoplasma gondii?* An opinion. *Parasitology Research* 86, 169-178.

Payne S & Ellis J. (1996) Detection of *Neospora caninum* DNA by the polymerase chain reaction. *International Journal for Parasitology* 26, 347-351.

Schares G, Heydorn A O, Cüppers A, Conraths F J & Mehlhorn H. (2001) *Hammondia heydorni*-like oocysts shed by a naturally infected dog and *Neospora caninum* NC-1 cannot be distinguished. *Parasitology Research* in press.

Shirley M W & Bedrnik P. (1997) Live attenuated vaccines against avian coccidiosis-success with precocious and egg-adapted lines of Eimeria. *Parasitology Today* 13, 481-484.

Speer C A, Dubey J P, McAllister M M, et al. (1999) Comparative ultrastructure of tachyzoites, bradyzoites, and tissue cysts of *Neospora caninum* and *Toxoplasma gondii*. International Journal for Parasitology 29, 1509-1519.

Stenlund S, Bjorkman C, Holmdahl O J M, Kindahl H & Uggla A. (1997) Characterisation of a Swedish bovine isolate of *Neospora caninum*. *Parasitology Research* 83, 214-219.

Thilsted J P & Dubey J P (1989) Neosporosis-like abortions in a herd of dairy cattle. *Journal of Veterinary Diagnostic Investigation* 1, 205-209.

The invention claimed is:

1. A *Neospora caninum* isolate isolated from the central nervous system of a dairy calf, the isolate having AGAL Accession No. NM01/22338, and wherein the isolate is naturally attenuated in its ability to cause neosporosis in a laboratory animal.

2. An isolated host cell infected with the *Neospora caninum* isolate as claimed in claim 1.

3. The host cell as claimed in claim 2 having AGAL Accession No. NM01/22339.

4. A vaccine composition comprising the *Neospora caninum* isolate as claimed in claim 1.

5. A method for inducing protective immunity against neosporosis caused by *Neospora caninum* in cattle or mice, the method comprising administering to the cattle or the mice the vaccine composition as claimed in claim 4.

6. The method as claimed in claim 5, wherein the protective immunity is induced in a cow.

7. A vaccine composition comprising the isolate as claimed in claim 1, wherein the isolate is in the form of a live isolate.

8. A method of detecting IgG antibodies to the *Neospora caninum* isolate of claim 1 in a serum sample from cattle or mice infected with said isolate comprising assaying the serum sample for IgG antibodies to the *Neospora caninum* isolate by ELISA.

* * * * *